United States Patent [19]
Albert

[11] Patent Number: 6,017,499
[45] Date of Patent: Jan. 25, 2000

[54] APPARATUS FOR CONTACTING SOLIDS IN THE FORM OF FREEFLOWING LUMPS WITH LIQUIDS OR GASES

[75] Inventor: Gert Albert, Brunsbuttel, Germany

[73] Assignee: RWE-DEA Aktiengesellschaft für Minepaloel und Chemie, Germany

[21] Appl. No.: 08/809,209

[22] PCT Filed: Nov. 4, 1995

[86] PCT No.: PCT/DE95/01552

§ 371 Date: Mar. 10, 1997

§ 102(e) Date: Mar. 10, 1997

[87] PCT Pub. No.: WO96/14150

PCT Pub. Date: May 17, 1996

[30] Foreign Application Priority Data

Nov. 8, 1994 [DE] Germany ............................ 44 39 860

[51] Int. Cl.[7] ...................................................... B01J 7/02
[52] U.S. Cl. ........................... 422/239; 422/209; 422/232
[58] Field of Search ..................................... 422/239, 232, 422/209

[56] References Cited

U.S. PATENT DOCUMENTS

| | | |
|---|---|---|
| 2,390,388 | 12/1945 | Rector . |
| 3,869,389 | 3/1975 | Rokitansky . |
| 5,139,953 | 8/1992 | Honda et al. ............................ 435/312 |
| 5,224,994 | 7/1993 | Daly . |

FOREIGN PATENT DOCUMENTS

| | | |
|---|---|---|
| 529297 | 11/1921 | France . |
| 2936023 | 3/1981 | Germany . |
| 149151 | 7/1985 | Germany . |
| 4026938 | 3/1991 | Germany . |
| 4336268 | 4/1994 | Germany . |
| 439238 | 12/1967 | Switzerland . |

*Primary Examiner*—Timothy McMahon
*Attorney, Agent, or Firm*—Bierman, Muserlian and Lucas

[57] ABSTRACT

The invention is directed to an apparatus for contacting in a reactor solids in the form of free-flowing lumps with liquids or for contacting solids with liquids and gases by bringing the reactants into contact with each other, said reactor comprising a housing containing a screen in the area of which contacting takes place wherein the screen is a rotary screen drum 5, the screen drum 5 rotates in a bottom vat during the operation, said vat holding a gaseous or liquid medium reacting with the solids, and the bottom vat 10 can be lowered such that the solids in the screen drum 5 and the medium in the bottom vat 10 can be separated from each other whenever it is desired to alter or interrupt the chemical reaction or physical process.

12 Claims, 4 Drawing Sheets

APPARATUS FOR CONTACTING SOLIDS IN THE FORM OF FREEFLOWING LUMPS WITH LIQUIDS OR GASES

The instant invention relates to an apparatus for contacting in a reactor solids in the form of free-flowing lumps with liquids or gases by bringing the reactants into contact with each other, said reactor comprising a housing containing a screen in the area of which contacting takes place.

DE 32 44 972 C1 discloses a process and an apparatus for the continuous production of aluminium alcoholates, comprising a reactor with a housing provided with a basketlike perforated plate bearing a packing of comminuted aluminium particles, e.g. in the form of needles. The screen basket forms the reaction zone located above a vat. It is necessary to keep the aluminium particles in the reaction zone suspended in order to achieve sufficiently high conversion rates. This is achieved by continuously pumping a very large quantity of liquid (alcoholate) through lines into the vat and further through the screen plate of the basket positioned above said vat into the reaction zone. A large quantity of the liquid pumped into the vat drains through the perforated bottom of the vat into the pump receiver. Liquid that has reached the reaction zone drains through the lateral walls of the basket. Vigorous recirculation of the liquid in combination with draining through the perforated vat and flowing back into the pump receiver constitutes a significant waste of energy. In order to maintain the amount of fluidising liquid charged from below through the screen plate in an economically desirable order, it is required that the metal particles to be dissolved be very small. Normally, metal particles in needle form are used which, for example, have lengths of 5 to 12 mm and diameters of 0.5 to 0.8 mm. Otherwise, the metal particles will sediment very rapidly and will clot on the bottom of the basket-like screen whereby most or all of said screen would be plugged and the reactor would have to be shut down.

Another disadvantage of the known reactor is the very expensive manufacture of the small, needle-like metal particles. Furthermore, due to the necessity of recirculating enormous quantities of liquid and of dividing up said feed quantity into one portion to be charged to the upper section and the other portion to be fed to the lower section, requiring considerable energy and capital expenditure, operation of the known reactor is disadvantageous. In case of malfunction of the known reactor, e. g. soiling of the screen, complete and rapid separation of the reactants from each other is impossible. Therefore, control of the exothermic reaction of aluminium with alcohol cannot be guaranteed.

DE 40 26 938 A1 describes a revolving column reactor comprising a perforated screen drum. Said reactor is used for obtaining substances by adsorption. Said patent specification does not describe a reaction aiming to dissolve solids, particularly aluminium lumps, by means of alcohol and the special problems presented thereby.

It is the object of the instant invention to provide an apparatus for dissolving solids as described hereinabove which allows more economic and safer operation.

According to the instant invention, there is provided an apparatus wherein
  the screen is a rotary screen drum,
  the screen drum rotates in a bottom vat during the operation, said vat holding a gaseous or liquid medium reacting with the solids, and
  the bottom vat can be lowered such that the solids in the screen drum and the medium in the bottom vat can be separated from each other whenever it is desired to alter or interrupt the reaction.

In addition to the dissolution of solids, chemical reactions or physical operations, e. g. catalytic treatment, inoculation, dyeing, disinfection, adsorption, heat treatment, low-temperature treatment and/or mixing may be performed in said apparatus.

When using a rotary screen drum, there is no need to recirculate large quantities of reaction liquid. Said screen drum recirculates the solids whereby complete contacting with the gaseous or liquid medium in the reactor or in the vat is ensured. It is no longer necessary to keep the solids suspended by whirling up. Now, significantly larger solids may be used, e. g. in the form of pellets, cubes, rectangular lumps or even larger pieces such as cut-offs of commercially available ingots or entire ingots having total weights of up to 25 kg. Such solids can be produced at considerably lower costs, and whole ingots are even available without additional cost. Since it is no longer necessary to vigorously recirculate the medium and to employ expensive solids, it is possible to work more economically. The possibility of lowering the bottom vat allows rapid separation of the reactants in the reaction zone. The degree of separation may be chosen between 0 and 100% thus allowing more sensitive control of the reaction and significant improvement of the operational reliability.

The revolving screen drum provides a completely permeable reaction zone in the drum. In the lower section of the reactor housing, the liquid can flow from the bottom vat into the drum and back into the vat, while in the upper section, the reaction gases and vapours can be led from the drum into the reactor housing and further to cooling or condensation. If the medium is alcohol, the reaction product is hydrogen. Alcohol vapour serves as a medium for removing the heat produced during the strongly exothermic reaction. The reaction liquid charged into the drum may permeate at any point of the drum wall.

The liquid free cross-section in the upper half of the screen drum shall be sufficiently large so that extremely large quantities of gas and vapour can run off.

Another advantage of said apparatus is attributable to the fact that the reaction volume may be adjusted to the throughput or to the reaction rate of the solids by simply extending the drum or by vertically shifting the bottom vat.

Another embodiment of the invention provides for a lance extending into the screen drum whereby fresh medium can be supplied either evenly over the total length of the drum or selectively to certain drum sections, thus triggering a particularly rapid reaction in the internal drum.

Another embodiment of the invention provides for two screen drums which are concentrically fitted into one another, the slot widths of the screens of the internal drum being larger than those of the external drum. It is thus possible to preheat the solids and to start their decomposition in the internal drum by eroding their surfaces until they drop through the slots of the internal drum into the external drum where they are completely dissolved. When using large solids, the internal drum also provides mechanical protection of the finer, external screens.

According to another embodiment of the invention, the solids may be charged through the drum shaft into the drum, thus allowing continuous, smooth feeding.

According to another embodiment of the invention, blades for circulating the solids are mounted inside the drum, thus allowing improved horizontal and vertical circulation of the solids in the rotating screen drum and providing even distribution.

Another embodiment of the invention provides for a row of nozzles through which the cleaning medium may be sprayed onto the outer side of the screen drum. Each section of the revolving screen drum moves past the nozzles through which the cleaning medium is sprayed under high pressure, thus allowing optimum cleaning of the screen drum. The external drum is continuously cleaned during operation so that it is no longer necessary to stop or even demount the apparatus for cleaning purposes. The amount of medium sprayed onto the drum depends on how much of the agent has to be added to sustain reaction and cooling. Hence, the cleaning or rinsing liquid also serves as a reactant and coolant.

Another embodiment of the invention provides for freely movable grinding media inside the drum. Said grinding media may be spheres, cubes or cylinders made of any material that is resistant to the medium. The solids in the screen drum are subjected to grinding by mere rotation of the drum. When employing said grinding media, grinding and rate of dissolution are favourably influenced due to improved surface activation resulting in a higher reaction rate during operation.

According to another embodiment of the invention, there is provided a rope winch for lowering the bottom vat. According to a further aspect of said embodiment, there is provided a hydraulic hoist for hoisting and lowering the bottom vat. In case of malfunction, rapid shutdown by lowering the bottom vat is very important. The reaction may be controlled by gradually lowering the vat. It is essential that in case of emergency the bottom vat can be lowered either hydraulically or by means of a rope winch without the necessity of using an aid for releasing the brake (not depicted), thus achieving rapid separation of medium and solids resulting in termination of the reaction.

According to another embodiment of the invention, the bottom vat is tiltable by swivelling around a shaft which is in parallel to the drum shaft. According to said embodiment which is particularly interesting from the aspect of construction, the means used for lowering the vat are only required on one side of the bottom vat.

According to another embodiment of the invention, the reactor housing cross-section comprises an upper and a lower semi-cylindrical dish, the edges of the dishes being interconnected by walls, i. e. the housing is extended in the direction in which the bottom vat can be lowered. However, due to the pressure occurring in the housing it may be necessary to improve the rigidity of the housing. In that case, a further aspect of said embodiment provides that the cross-section of the reactor housing be cylindrical.

Another embodiment of the invention provides for cylindrical screen drums, but polygonal drums would also be appropriate.

According to another embodiment of the invention, the reactants, i. e. solids and gaseous or liquid media, are fed in a counter-current, co-current or cross-current mode through the hollow shaft ends into the screen drum.

According to another embodiment of the invention, the solids recirculated in the screen drum are capable of reacting with the gaseous medium in the reactor.

Another embodiment of the invention provides that, for the production of metal alcoholates, solids in the form of free-flowing lumps made of aluminium, magnesium or silicon in straight form, as mixtures or as alloys are brought into contact in the screen drum with $C_1$ to $C_{12}$ alcohols in pure form or as mixtures. In the special case of aluminium alcoholate production solids made of aluminium in the form of free-flowing lumps are contacted in the screen drum with $C_1$ to $C_{12}$ alcohols in pure form or as mixtures.

Another embodiment of the invention provides that for the production of aluminium alcoholates solid aluminium in the form of free-flowing lumps is contacted in the screen drum with aliphatic $C_2$ to $C_{10}$ alcohol in pure form or as mixtures, preferably with $C_5$ to $C_8$ alcohol in pure form or as mixtures, more particularly with $C_6$ alcohol.

The instant invention will be described in greater detail hereinafter with reference to the attached drawings, wherein.

Figure 6:
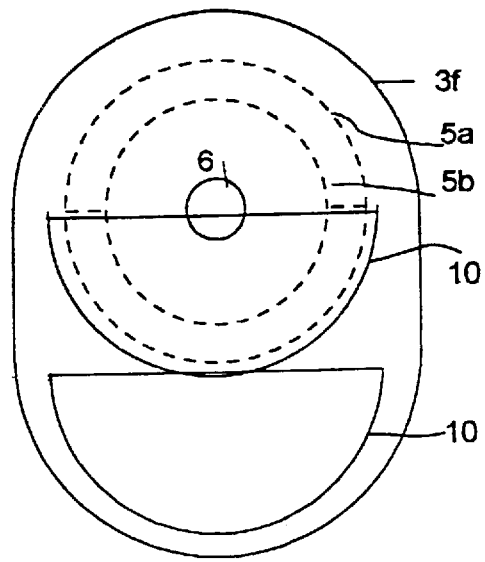
Figure 7:
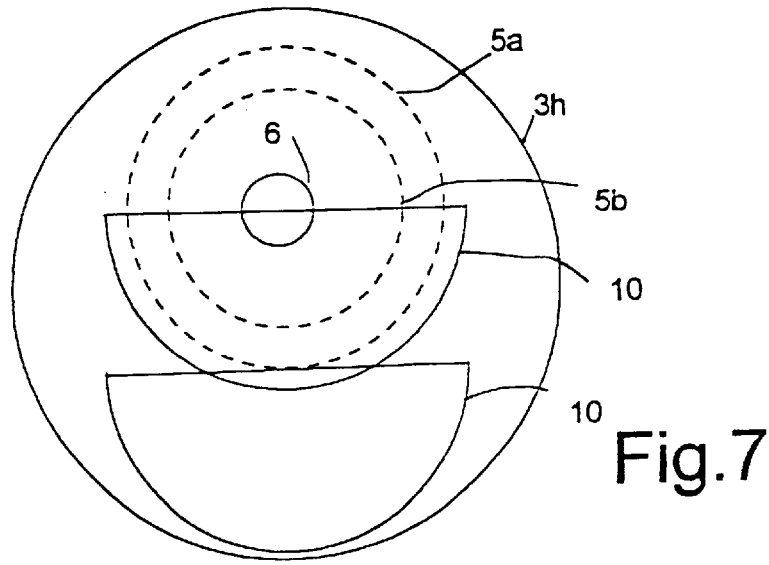
Figure 8:
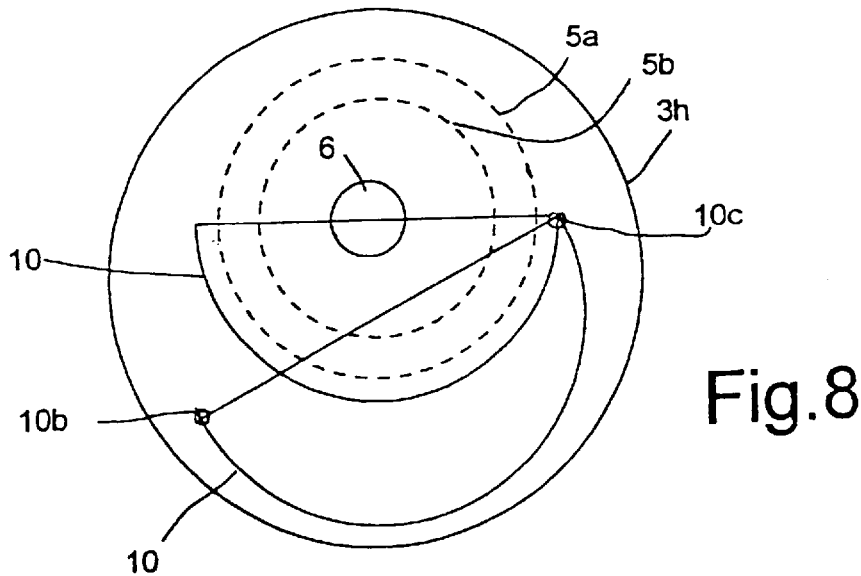

FIG. 6, FIG. 7, FIG. 8 outline variants of lowering of the bottom vat.

Figure 9:
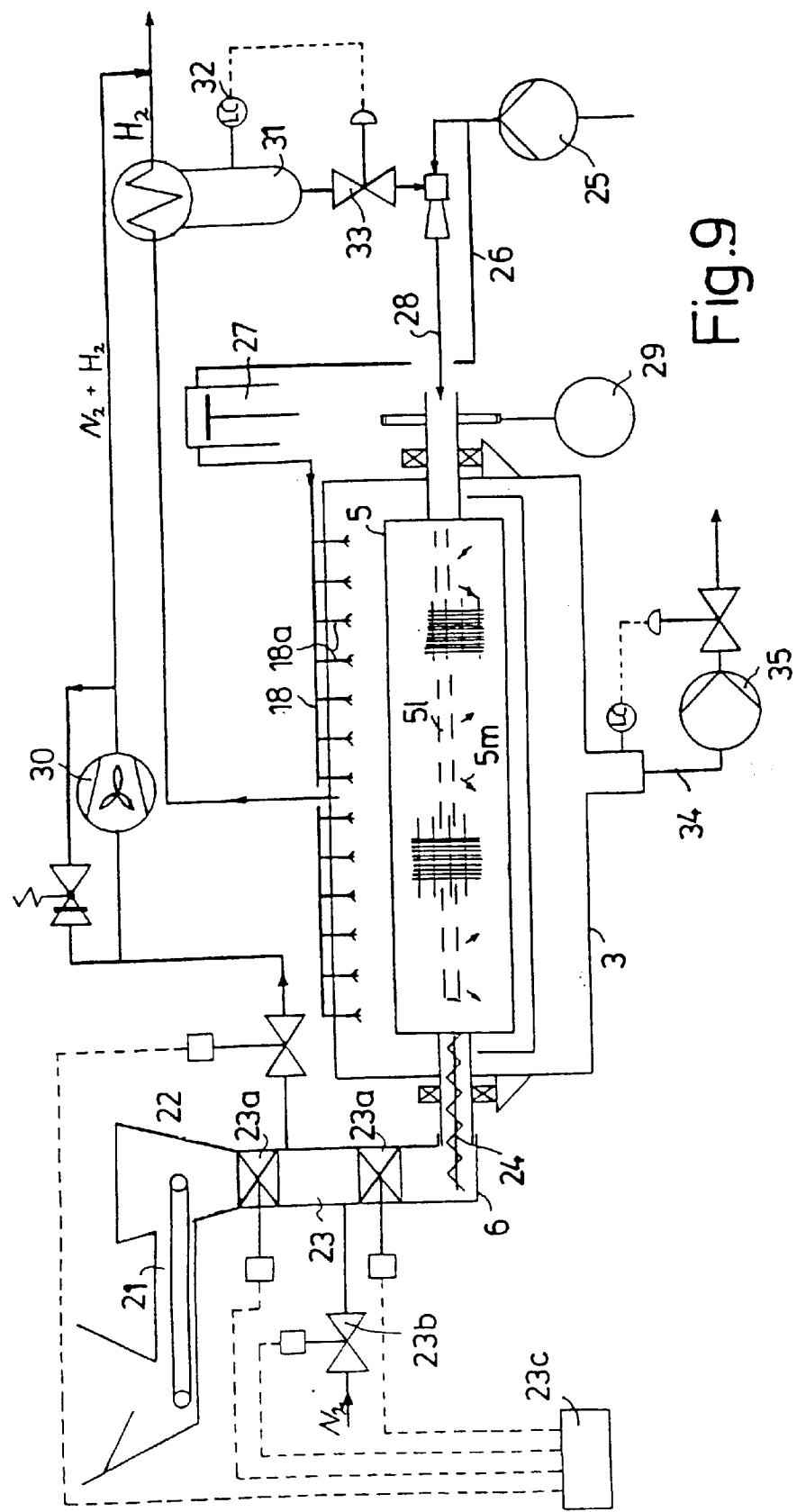

FIG. 9 illustrates the arrangement of the apparatus in accordance with FIGS. 1 through 8. In general, the apparatus according to the invention serves the purpose of promoting a reaction between solids which are present in the form of lumps and a gaseous or liquid medium, said medium being capable of dissolving the solids. Preferred materials for the solids are aluminium, magnesium or silicon, but other materials may also be employed. A suitable gaseous or liquid medium is any medium that is capable of dissolving said solids. When using liquid media, particularly straight chain or branched $C_1$ to $C_{12}$ alcohols, polyhydric $C_2$ to $C_{12}$ alcohols, cyclic and aromatic, mono- or polyhydric alcohols are appropriate. The following description of one embodiment of the instant invention relating to the production of aluminium alcoholates from aluminium lumps and alcohol shall be considered as an example and is not to be construed as limiting the instant invention.

Figure 1:
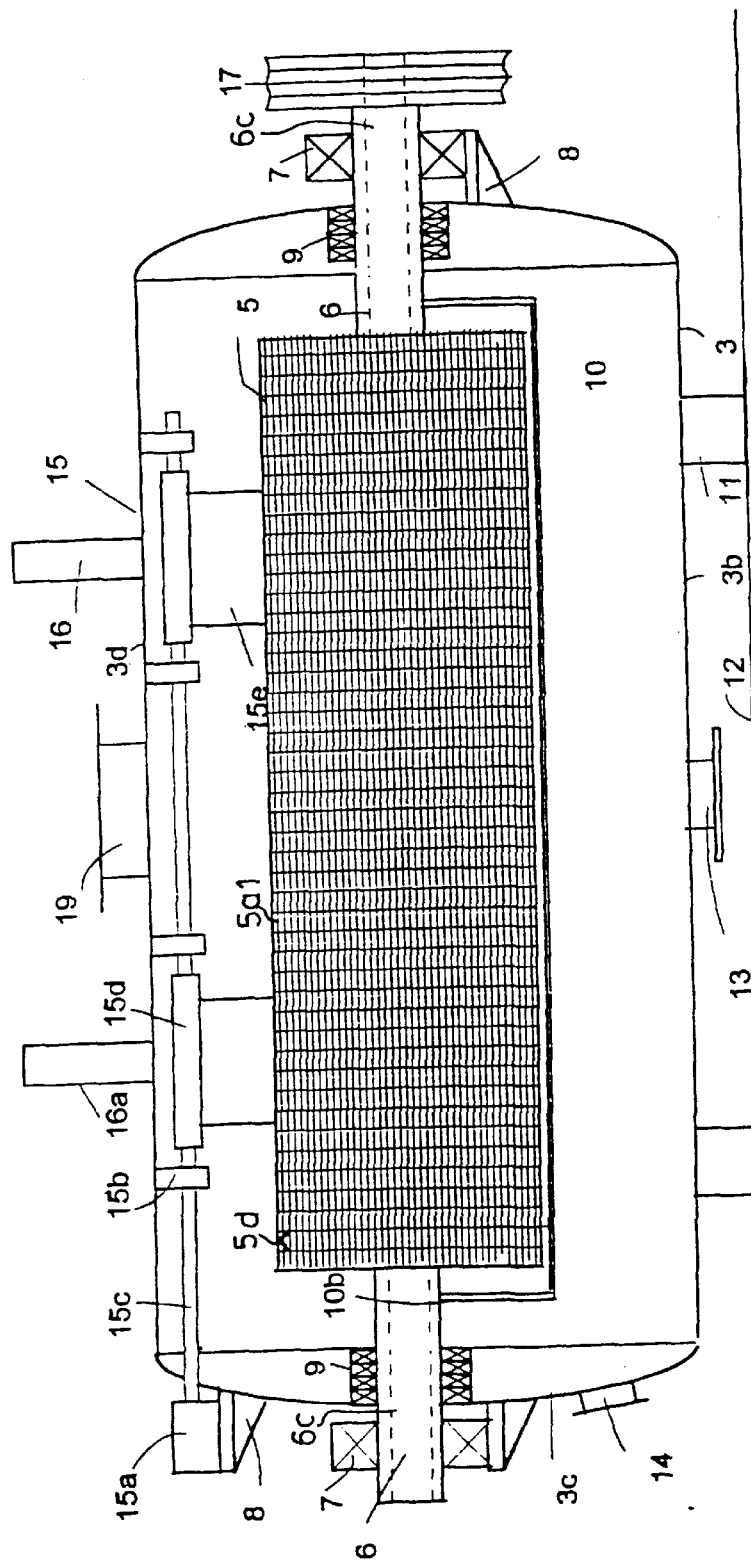
FIG. 1 is an apparatus for producing metal alcoholates comprising a screen drum promoting the reaction between aluminium and alcohol.

FIG. 1 outlines an apparatus for producing aluminium alcoholates wherein the reactor has a housing 3 the front wall of which 3a (depicted in FIG. 2) is not shown in order to illustrate the interior of the reactor housing 3. Inside the reactor housing 3 there is a screen drum 5. The shaft 6 of said screen drum 5 is running in bearings 7 supported by struts 8 mounted on the reactor housing 3. The two shafts 6 protruding through packings 9 from the reactor housing 3 are hollow.

Figure 2:
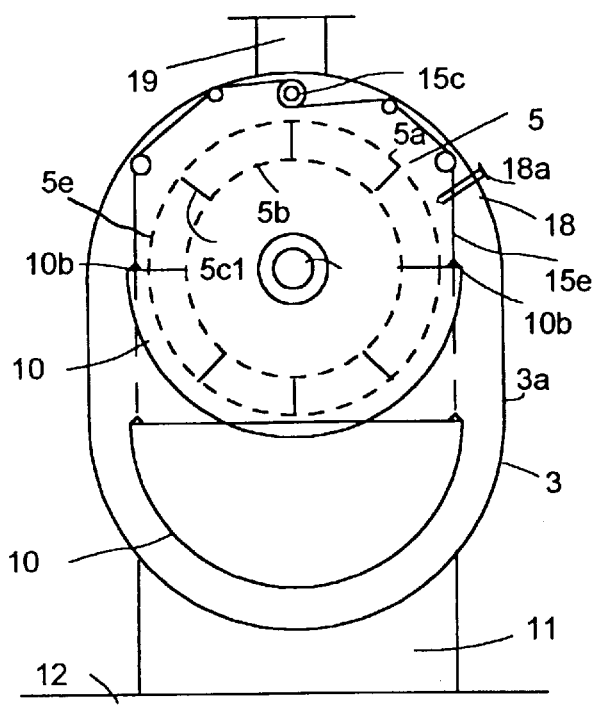
FIG. 2 illustrates the lowering of the vat inside the housing of said apparatus by means of a rope winch.

As shown in FIGS. 1 and 2, the lower half of the screen drum 5 is positioned in a bottom vat 10. Said bottom vat 10 which is depicted in FIG. 1 in a slightly hoisted position can be lowered such that, on the one hand, the alcohol or the aluminium alcoholates obtained by reacting aluminium with alcohol and, on the other hand, the aluminium lumps in the screen drum 5 can be completely separated from each other.

The reactor housing 3 is supported by feet 11 standing on the ground 12. On the bottom side 3b of the reactor housing, there is provided an outlet 13 for liquid. In the left wall 3c of the reactor housing 3, there is provided a manhole 14.

Figure 3:
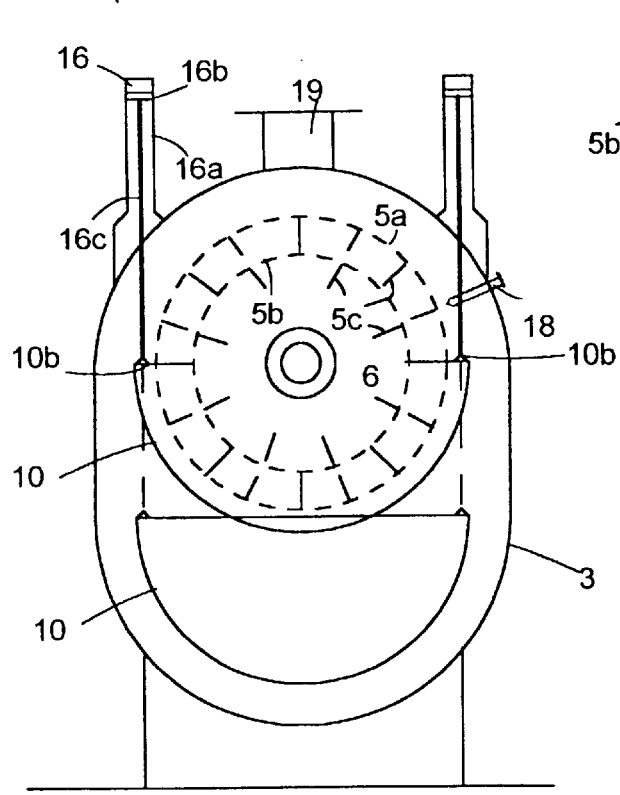
FIG. 3 depicts the lowering of the vat inside the apparatus by means of hydraulic cylinders.

The rope winch 15 and the hydraulic hoist 16 which may be used for lowering and hoisting the bottom vat 10 are depicted in FIG. 2 and FIG. 3, respectively. The rope winch 15 comprises a motor 15a mounted on a support outside the reactor housing 3. The rope winch shaft 15c running in bearings 15b and driven by the motor 15a is positioned on the upper side 3d of the reactor housing 3. It essentially extends over the entire reactor housing 3. Ropes 15e hanging down from the winding devices 15d grip the bottom vat 10 at its upper edge 10b. There is also provided a rope brake (not depicted) permitting to arrest the ropes 15e holding the bottom vat 10 in order to maintain the bottom vat 10 in the lifted position.

FIG. 3 illustrates the hydraulic hoist 16 for the bottom vat 10. Said hydraulic hoist comprises several cylinders 16a with pistons 16b and rods 16c whereby the vat can be gripped at its upper edge 10b.

Figure 5:
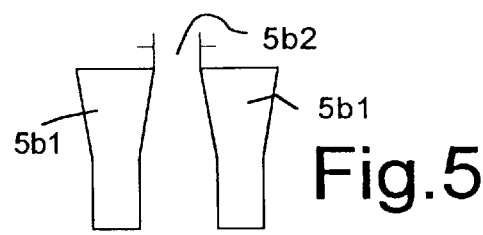
FIG. 4 and FIG. 5 are sectional views of the internal and external bridges of the screen drums with different slot widths.
Figure 4:
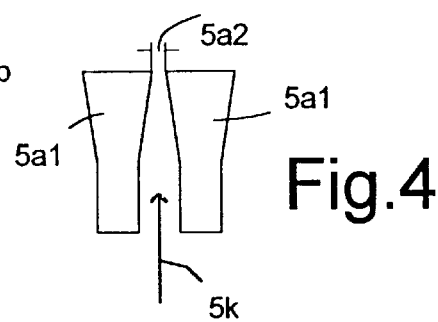

Screen drum 5 comprises an external screen drum 5a or, optionally, two concentric screen drums, i. e. an external drum 5a and an internal drum 5b. Screen drums 5a and 5b comprise a support consisting of longitudinally and transversely profiled bridges designed such that they can hold perforated plates 5a1, 5b1 and mixing blades 5c. The perforated plates 5a1 and 5b1 are interconnected by means of bridges (not depicted) such that lattices are formed whereby the aluminium lumps to be processed are held within the screen drum 5. The two screen drums 5a and 5b are interconnected by means of supporting bars 5c1. FIGS. 4 and 5 are sectional views of the longitudinal bridges 5a1 and 5b1. Each figure illustrates a pair of bridges positioned side by side. FIG. 4 depicts two longitudinal bridges of the external screen drum 5a, while FIG. 5 shows two longitudinal bridges of the internal screen drum 5b. The longitudinal bridges 5a1 of the external screen drum are provided with slots 5a2 having widths of from 0.2 to 0.4 mm, preferably 0.3 mm.

The slots 5b2 between the longitudinal bridges 5b1 of the internal screen drum 5b have widths of from 10 to 50 mm. The cleaning liquid is injected in the direction indicated by the arrows 5k, the slots 5a2 thus being well cleaned.

FIG. 6 shows an elongated reactor housing 3 in cross-sectional and sectional views. Said housing comprises two cylindrical semidishes 3f interconnected by means of walls 3a. In the reactor housing 3 the height of which is extended according to this figure, a bottom vat 10 can be lowered to such an extent that it is completely withdrawn from the sphere of activity of the aluminium lumps in the screen drum even if the screen drum has a large diameter.

For higher pressures the cylindrical reactor housing 3h depicted in FIGS. 7 and 8 will be more appropriate.

FIG. 8 illustrates an embodiment of the invention wherein a cylindrical reactor housing 3h is employed. However, in contrast to FIGS. 6 and 7, the vat 10 is not lowered vertically, but can be tilted around a shaft 10c extending parallel to the drum shaft 6. When mounting the vat 10 in that way, lifting will be facilitated, both by hydraulic means 16 and rope winch 15 because it will only be necessary to hoist or lower the vat at a single edge 10b. The tiltable edge may be provided with a jagged weir in order to ensure smooth and regular draining from the vat.

During operation the screen drum 5 is set in rotation by means of a pulley 17. Aluminium in the form of pellets, cubes or rectangular lumps or even larger pieces such as ingot cut-offs or entire ingots are charged through one or both hollow shafts 6 into screen drum 5 from where they fall into the wide-meshed internal drum 5b. It is also possible to introduce the reactants, i. e. aluminium lumps and alcohol, in a counter-current configuration through the two hollow shafts into the screen drum 5. $C_1$ to $C_{12}$ alcohol is charged through inlet 19 into the reactor housing, the mixture of aluminium lumps and alcohol thus reaching the lower half of the screen drum enclosed by the vat 10. During the process, while the screen drum 5 is rotating, the aluminium lumps gradually dissolve until they are small enough to drop from the internal drum 5b into the external drum 5a provided with narrower slots. Due to the narrower slots 5a2 in the external drum 5a, there is the risk of plugging. In order to prevent plugging of said slots, there is provided a row of nozzles 18 comprising several nozzles 18a distributed over the total length of the screen drum 5. Alcohol is sprayed under high pressure through each of said nozzles onto the outer side of the external wall of the screen drum 5a, the screen drum 5 thus being constantly cleaned during operation.

The layout according to FIG. 9 shows reactor housing 3, screen drum 5 and bottom vat 10. The aluminium particles are charged into a hopper 22 by means of a feeder 21. The aluminium particles leaving the hopper reach a gate 23 provided with cut-off valves 23a which are arranged in series at some distance to each other and which are controlled by a gate control 23c. The gate is used whenever excess pressure or harmful or inflammable gases or vapour are employed in the process. Said gate may be flushed, e. g. with nitrogen or by another inert gas, via valve 23b. After passing the gate 23 the aluminium particles reach the hollow shaft 6 from where they are transported into the screen drum 5 by means of a screw conveyor 24. The fixed gate 23 and the rotating shaft 6 are connected with each other via a rotating packing. Fresh alcohol is fed into the apparatus by means of pump 25. Line 26 leads to another pump 27 injecting the alcohol under high pressure via a flushing line 18 through nozzles 18a into the drum 5. For the first filling or for refilling, the fresh alcohol may also be charged in the direction indicated by arrow 28, i. e. through shaft 6 into drum 5, by means of a lance 51, thus permitting even distribution illustrated by little arrows 5m.

Drum 5 is rotated by means of a motor 29. Hydrogen and alcohol vapours which are formed in the process are sucked off through inlet 19 into the condenser with liquid collector 31. The alcohol vapours are condensed and thereafter recycled to the process, e. g. in the direction indicated by arrow 28. The effluent from pump receiver 31 being level-controlled by means of a sensor 32 actuating discharge valve 33. The aluminium alcoholate is discharged through line 34 by means of pump 35. Vapour and gases from gate 23 are sucked off by blower 30 and are reused for example by feed into the hydrogen stream downstream of the condenser.

The embodiment of the instant invention describes a continuous process. However, the example is also applicable to a discontinuous process, e. g. whenever it is desirable to interrupt the reaction in order to continue with a different medium than the one employed at the beginning or to switch from liquid-phase to gaseous-phase operation. Vat and/or drum may be provided with heating tubes in order to accelerate the reaction, while cooling, e. g. by introducing cooling liquid into the heating tubes, would be appropriate to reduce the reaction rate.

The reaction temperature may be monitored by means of a measuring instrument (not depicted) mounted in the bottom vat 10.

I claim:

1. An apparatus for bringing solids in the form of pourable pieces into contact with fluids or for bringing solids into contact with fluids and gases in a reactor by guiding the reactants together, the reactor comprising a reactor housing with a screen support in the reactor housing and, in this latter, a screening support in the area of which the contacting takes place, wherein the screening support is constructed as a rotating, concentric screening drum (5) mounted on at least one hollow shaft (6) provided with means (29) for transporting solids through the hollow shaft(s) into the drum (5) interior;

the screening drum (5) is, when in operation, rotatable in a bottom tank (10) in which there is a gaseous or liquid medium which reacts with the solids, and the bottom tank (10) can be lowered until such time as the solid pieces in the screening drum (5) and the medium in the bottom tank (10) can be separated from each other to vary the degree of or to interrupt the chemical reaction or the physical process by the lowering of the bottom tank (10).

2. The apparatus of claim 1 wherein circulating blades (5*c*) for the pieces of solids are provided in the interior of the drum.

3. The apparatus of claim 1 wherein a jet bar (18) is provided whereby the cleaning medium can be sprayed onto the outside (5*e*) of the screening drum (5*a*).

4. The apparatus of claim 1 wherein freely movable grinding members are provided in the drum interior.

5. The apparatus of claim 1 wherein a cable-operating lifting device (15) is provided for lowering the bottom tank (10).

6. The apparatus of claim 1 wherein a hydraulic lifting device (16) is provided for lowering the bottom tank (10).

7. The apparatus of claim 1 wherein the bottom tank (10) can be tiltingly lowered by pivoting about a shaft (10*c*) parallel with the drum shaft (6).

8. The apparatus of claim 1 wherein in cross-section the reactor housing (3) consists of an upper and a lower hemicylindrical shell (3*f*) of which the shell edges are connected by connecting walls (3*a*).

9. The apparatus of claim 1 wherein the reactor housing (3*h*) is of cylindrical cross-section.

10. An apparatus for bringing solids in the form of pourable pieces into contact with fluids or for bringing solids into contact with fluids and gases in a reactor by guiding the reactants together, the reactor comprising a reactor housing with a screen support in the reactor housing and, in this latter, a screening support in the area of which the contacting takes place, wherein the screening support is constructed as 2 rotating, concentric screening drums (5*a*, 5*b*) mounted into one another on at least one hollow shafts (6) provided with means (29) for transporting solids through the hollow shaft(s) into the drum (5) interior;

the slot width of the screens on the inner screening drum (5*b*) being greater than the slot width of the screens on the outer screening drum (5*a*)

the screening drum (5) is, when in operation, rotatable in a bottom tank (10) in which there is a gaseous or liquid medium which reacts with the solids, and the bottom tank (10) can be lowered until such time as the solid pieces in the screening drum (5) and the medium in the bottom tank (10) can be separated from each other to vary the degree of or to interrupt the chemical reaction or the physical process by the lowering of the bottom tank (10).

11. The apparatus of claim 10, wherein there is introduced into the interior screening drum (5*b*), a lance (5*d*) by which fresh medium can be incorporated regularly over the entire drum length or into specific areas of the drum (5).

12. The apparatus of claim 10 wherein the screening drums (5*a*,5*b*) are of cylindrical or polygonal construction.

* * * * *